United States Patent [19]
Edelstam

[11] Patent Number: 5,977,143
[45] Date of Patent: Nov. 2, 1999

[54] MEDICAMENT AGAINST INFERTILITY WHICH REDUCES PHAGOCYTOSIS OF SPERMATOZOA IN WOMEN

[76] Inventor: Greta Edelstam, Saltängsvägen 2, 131 50 Saltsjö-Duvnäs, Sweden

[21] Appl. No.: 08/800,737

[22] Filed: Feb. 15, 1997

[51] Int. Cl.$^6$ .......................... A61K 31/445; A61K 31/16
[52] U.S. Cl. ............................................ 514/330; 514/626
[58] Field of Search ..................................... 514/330, 626

[56] References Cited

FOREIGN PATENT DOCUMENTS 8804214-8  11/1988  Sweden.

OTHER PUBLICATIONS

Medline Abstract, AN:95200153 (1995) Doherty, M.M. et al.
Gennaro, A.R. et al., Remington's Pharmaceutical Sciences (18$^{th}$ Ed.) (1990), Mack Pub. Co., Easton, PA., pp. 1048–1053, 805–806 and 820–821.
Publication in Favour (1) and Against (2) the Use of Lignocaine During Fertilisation; manuscript by Greta Edelstam, M.D., Ph.D.; May 15, 1997; 7 pages.
The Effect of Lignocaine on Sperm Phagocytosis in the Peritoneal Fluid From Women with and without Endometriosis; Greta A.B. Edelstam, M.D., Ph.D.; Eva Andersson; Arne Rådestad, M.D., Ph.D.; Folke Flam, M.D. Assoc. Prof; Claes Gottlieb, M.D. Assoc. Prof.; (1998), Hum. Reprod., 13(5), pp. 1353–1356.
Sperm phagocytosis by human peritoneal macrophages: A possible cause of infertility in endometriosis, Joseph J. Muscato, M.D.; A.F. Haney, M.D.; and J. Brice Weinberg, M.D., pp. 503 through 510, American Journal of Obstetric Gynecology; Nov. 1, 1982.
Hyaluronan and Myeloperoxidase in Human Peritoneal Fluid During Genital Inflammation, Greta A.B. Edelstam, Orjan Lundkvist, Per Venge, and Torvard C. Laurent; *Inflammation*, vol. 18, No. 1, 1994; pp. 13 through 21.
Role of Periotoneal Inflammation in Endometriosis–associated Infertility, Jouko Halme; *Annals New York Academy of Sciences*, pp. 266 through 275; (1991).
Pathophysiology of mild endometriosis: review of literature, Tahir A. Mahmood and Allan Templeton; *Human Reproduction*, vol. 5, No. 7, 1990, pp. 765–782.
Sperm survival studies in peritoneal fluid from infertile women with endometriosis and unexplained infertility by Makarand K. Oak, Eric N. Chantler, Catherine A. Vaughan Williams and Max Elstein; *Clinical Reproduction and Fertility*(1985) 3, pp. 297 through 303; (1985).
Peritoneal Fluid Cell Populations in Infertility Patients, A.F. Haney, M.D., Joseph J. Muscato, M.D., and J. Brice Weinberg, M.D.; *Fertility and Sterility*, vol. 35, No. 6, Jun. 1981, pp. 696, 697, and 698.
Semen preparation with the Sperm Select system versus a washing technique, Elizabeth R. Zimmerman, M.D., Kathryn R. Robertson, B.S., Helen Kim, B.S., Erma Z. Drobnis, Ph.D., and Steven T. Nakajima, M.D.; *Fertility and Sterility*, vol. 61, No. 2, Feb. 1994; pp. 269 through 275.

An ovum capture inhibitor (OCI) in endometriosis peritoneal fluid: an OCI–related membrane responsible for fimbrial failure of ovum capture, Hiroshi Suginami, J.D. and Kohji Yano, M.D., *The American Fertility Society*, vol. 50, No. 4, Oct. 1988, pp. 648 through 653.

Peritoneal macrophages and infertility: the association between cell number and pelvic pathology, David L. Olive, M.D., J. Brice Weinberg, M.D., and Arthur F. Haney, M.D.; *The American Fertility Society*, vol. 44, No. 6, Dec. 1985; pp. 772 through 777.

Preparation of pure hepatocytes and reticuloendothelial cells in high yield from a single rat liver by means of Percoll centrifugation and selective adherence, Bård Smedsrod and Håkan Pertoft; J. Leukocyte Biol., (1985), 38/2, pp. 213–230.

Peritoneal Macrophages From Patients With Endometriosis Release Growth Factor Activity in Vitro, J. Halme, C. White, S. Kauma, J. Estes, and S. Haskill; Journal of Clinical Endocrinology and Metabolism, vol. 66, No. 5, 1988, pp. 1044 through 1049.

The Effects of Lignocaine on Human Sperm Motility, Stephen John Bennett, Virginia Bolton, and John Parsons; *Journal of Assisted Reproduction and Genetics* vol. 9, No. 3, 1992; pp. 271 through 273.

Follicular fluid Lidocaine levels during transvaginal oocyte retrieval, Dwight D. Bailey–Pridham, M.D., Eli Reshef, M.D.; Kenneth Drury, Ph.D.; Christine L. Cook, M.D.; Harrell E. Hurst, Ph.D.; and Marvin A. Yussman, M.D.; *Fertility and Sterility*, vol. 53, No. 1, Jan. 1990; pp. 171, 172, 173.

Effect of peritoneal fluid on sperm motility and velocity distribution using objective measurements, Gianni Soldati, M.Sc.; Ana Piffaretti–Yanez, M.Sc.; Aldo Campana, M.D.; Maurizio Marchini, M.D.; Massimo Luerti, M.D.; Marco Balerna, Ph.D.; *Fertility and Sterility*, vol. 52, No. 1, Jul. 1989; pp. 113 through 119.

Toxicological Assessment of Lidocaine in the Pregnant Rat, L. J. Ramazzotto, F. A. Curro, J.A. Paterson, P. Tanner, and M. Coleman; *J. Dent Res*, vol. 64, No. 10; Oct. 1985; pp. 1214 through 1217.

*Primary Examiner*—M. Moezie
*Attorney, Agent, or Firm*—Fasth Law Offices; Rolf Fasth

[57] ABSTRACT

The present investigation relates to the use of a local anesthetic for the manufacture of a medicament for use against infertility or for increasing fertility. It also relates to a pharmaceutical composition comprising a pharmaceutically effective dose of a local anesthetic together with a pharmaceutically acceptable excipient. It also relates to a process for increasing fertility in a woman with said pharmaceutical composition.

5 Claims, 5 Drawing Sheets

MEDICAMENT AGAINST INFERTILITY WHICH REDUCES PHAGOCYTOSIS OF SPERMATOZOA IN WOMEN

TECHNICAL FIELD

The present invention relates to the use of a local anesthetic for the manufacture of a medicament for use against infertility or for increasing fertility. It also relates to a pharmaceutical composition comprising a pharmaceutically effective dose of a local anesthetic together with a pharmaceutically acceptable excipient. It also relates to a process for increasing fertility in a woman with said pharmaceutical composition.

BACKGROUND OF THE INVENTION

Infertility or subfertility could be a problem for people afflicted therewith. A common treatment of infertile women is IVF (in vitro fertilization) treatment. The basis of the IVF treatment is as follows:

Stimulation of ovulation: Daily hormonal injections, ultrasound examinations and blood samples.

Oocyte retrieval: Ultrasound guided ovarian punctures performed vaginally in local anesthesia.

Preparation of spermatozoa: Swim-up, swim-down, sperm select or other methods to select the optimal population with the best progressive motility.

In vitro fertilization: Incubation of oocytes and the selected population of spermatozoa in a cell incubator. Direct microscopic inspection of cell division and selection of the most vital blastocyte.

Embryo transfer: 2–3 blastocytes with the best vitality is deposited in the uterine cavity for hopeful implantation in the endometrium.

IVF treatment is an expensive method that for some couples initiates complicated psychological side effects. The technical and artificial way of trying to become pregnant has the disadvantages for the couple going through the treatment which may adversely affect the relationship. After all the troublesome treatment there is only a pregnancy rate of 25–30%, leaving those who did not succeed with a damaged relationship and still no child. The cost for IVF treatment is around 20 000–25 000 SEK per menstrual cycle.

In spite of several previous investigations the reasons for infertility during endometriosis is not clear and neither is the lack of improved fertility rate after treatment. Particularly the relationship is unclear between mild endometriosis and subfertility in the absence of pelvic adhesions (Mahmood, T A, Templeton A. Patophysiology of mild endometriosis: review of literature. Human Reproduction 1990; 5:765–784).

Increased numbers of leukocytes has been found in the peritoneal fluid (PF) from patients with endometrial peritoneal implants and has been considered as an ongoing sterile inflammation (Haney A F, Muscato J J, Weinberg J B: Peritoneal fluid cell populations in infertility patients. Fertil Steril 1981, 35:696–698; Edelstam GAB, Lundkvist O E, Venge P, Laurent T C: Hyaluronan and myeloperoxidase in the peritoneal fluid during genital inflammation. Inflammation 1994, 18:13–21). The increased number of leukocytes contain in vivo primed macrophages secreting a macrophage derived growth factor (MDGF) that may explain the proliferation of the endometrial tissue (Halme J, White C, Kauma S, Estes J, Haskill S. Peritoneal macrophages from patients with endometriosis release growth factor activity in Vitro. J Clin Endocrin and Metabolism. 1988;66:1044–49). Other secretory products from the macrophages, growth factors such as TNF and interferon, exhibit gamete toxicity and may also have an adverse impact on the fertility process (Halme J: Role of peritoneal inflammation in endometriosis-associated infertility. Ann N Y Acad Sci 1991; 622:266–74).

Also the cell-free peritoneal fluid is of importance in the reduced fecundity since it has been shown that it significantly reduces the ovum pick up capacity of the fimbriae of the fallopian tubes (Suginami H, Yano K, Watanbe K, Matsnura S: A factor inhibiting ovum capture by the oviductal fimbriae present in endometriosis peritoneal fluid. Fertil Steril 1986; 46:1140–1146). In peritoneal fluid from patients with endometriosis and unexplained infertility respectively a reduced progressive velocity of spermatozoa has been found (Makarand K, Oak M, Chantler E N, Vaughan Williams C A, Elstein M. Sperm survival studies in peritoneal fluid from infertile women with endometriosis and unexplained infertility. Clinical reproduction and fertility 1985; 3:297–303.). Even more interesting is the increased phagocytosis of spermatozoa that has been found during incubations for 24 h in vitro with peritoneal fluid from patients with endometriosis (Muscato J J, Haney A F, Weinberg J B, Sperm phagocytosis by human peritoneal macrophages: a possible cause of infertility in endometriosis. Am J Obstet Gynecol 1982; 144: 503–510). In that particular study there were however several different sperm donors and therefore immunological factors involved cannot be excluded.

SUMMARY OF THE INVENTION

The present invention is an alternative method to the IVF treatment for fertilization of women. It has been found by in vitro studies that phagocytosis of spermatozoa is reduced by lidocaine. It is suggested that this effect of lidocaine is due to stabilization of the cell membrane by prohibiting the increase of $Na^+$ permeability and by probably interfering with ATP in the cell membrane. The cost for this treatment will be approximately 10% of the IVF treatment, e.g. 2 500 SEK per menstrual cycle. There is no technical fertilization process that can cause psychological side effects. This treatment can be tried in patients with endometriosis and/or slight mechanical cause of infertility. It can be carried out while waiting for IVF and does not affect the possibility of successful later IVF treatment.

So far no treatment of infertility with lidocaine is reported in the literature. However, other pharmaceutical effects of lidocaine are known. e.g. as in EP 507 160, which discloses an external preparation for application to the skin containing; lidocaine which comprises a drug-retaining layer placed on a support. The preparation should be used for treatment of herpes zoster neuralgia and postherpetic neuralgia.

BRIEF DESCRIPTION OF THE DRAWINGS

As used in the drawings "endometr" relates to endometriosis and "end-prob" relates to probable endometriosis.

FIG. 1 is a schematic illustration showing the number of free spermatozoa shown for each day of incubation: with cellmedium (A, control), with cellmedium and lidocain (B), with peritoneal fluid (C, control) and with peritoneal fluid and lidocain (D).

FIG. 2 is a schematic illustration showing the number of progressively moving spermatozoa shown for each day of incubation: with cellmedium (A, control), with cellmedium and lidocain (B), with peritoneal fluid (C, control) and with peritoneal fluid and cellmedium and lidocain (B), with peritoneal fluid (C, control) and with peritoneal fluid and lidocain (D).

FIG. 3 is a schematic illustration showing the number of non progressively but moving spermatozoa shown for each day of incubation: with cellmedium (A, control), with cellmedium and lidocain (B), with peritoneal fluid (C, control) and with peritoneal fluid and lidocain (D).

FIG. 4 is a schematic illustration showing the number of alive but stationary spermatozoa shown for each day of incubation: with cellmedium (A, control), with cellmedium and lidocain (B), with peritoneal fluid (C, control) and with peritoneal fluid and lidocain (D).

FIG. 5 is a schematic illustration showing the number of dead spermatozoa shown for each day of incubation: with cellmedium (A, control), with cellmedium and lidocain (B), with peritoneal fluid (C, control) and with peritoneal fluid and lidocain (D).

DETAILED DESCRIPTION

Figure 1A:
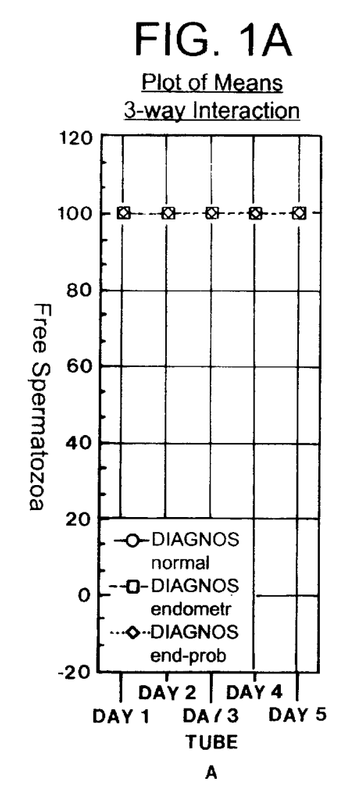
Figure 1B:
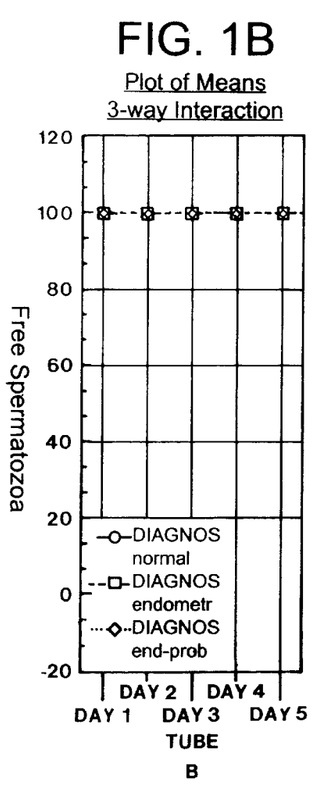
Figure 1C:
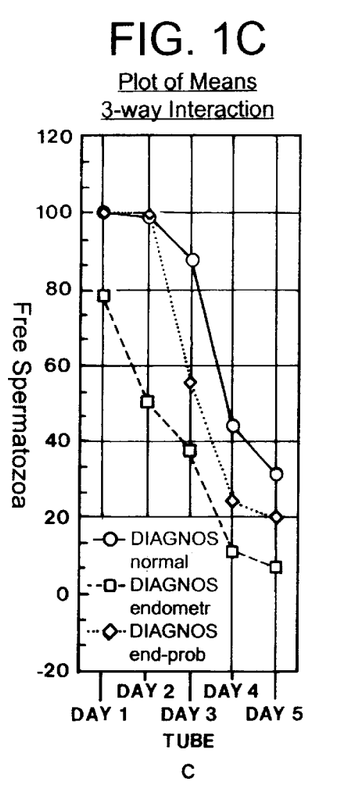
Figure 1D:
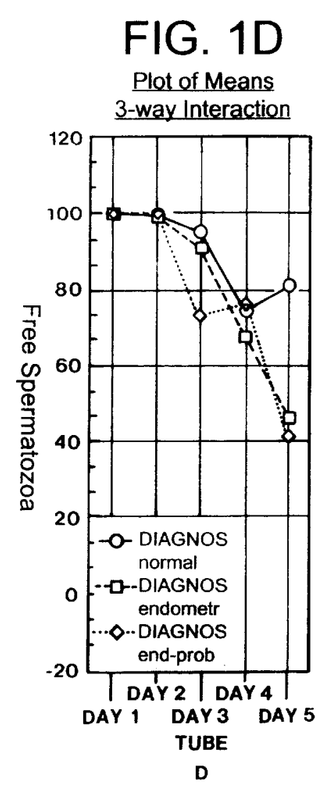
Figure 2A:
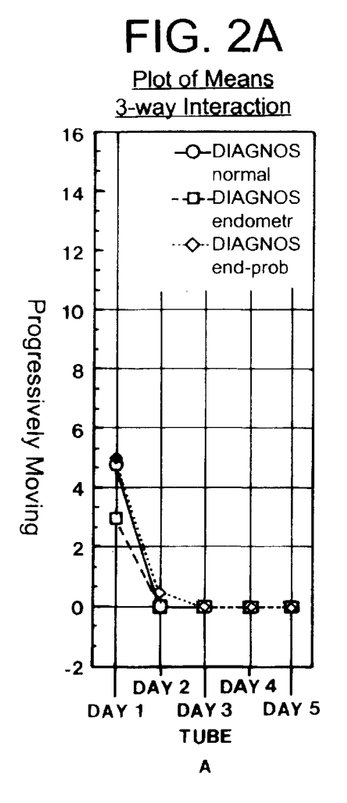
Figure 2B:
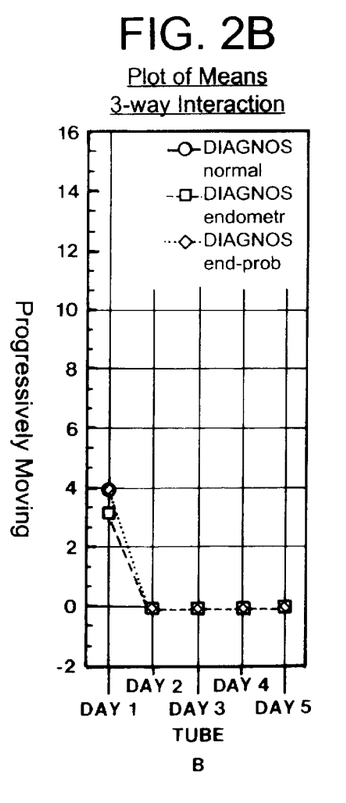
Figure 2C:
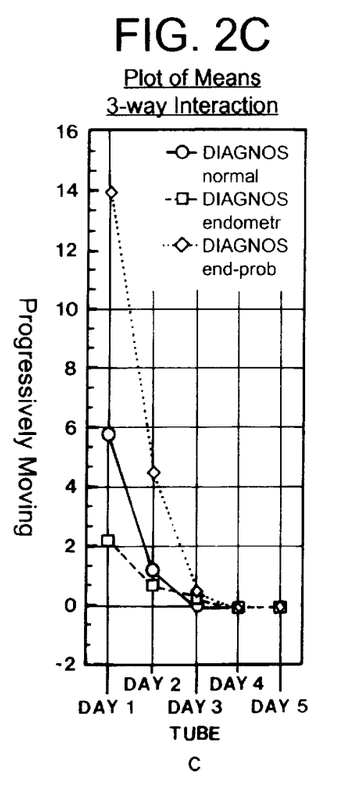
Figure 2D:
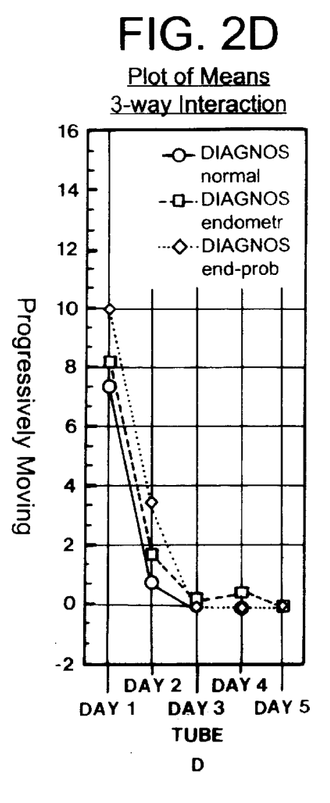
Figure 3A:
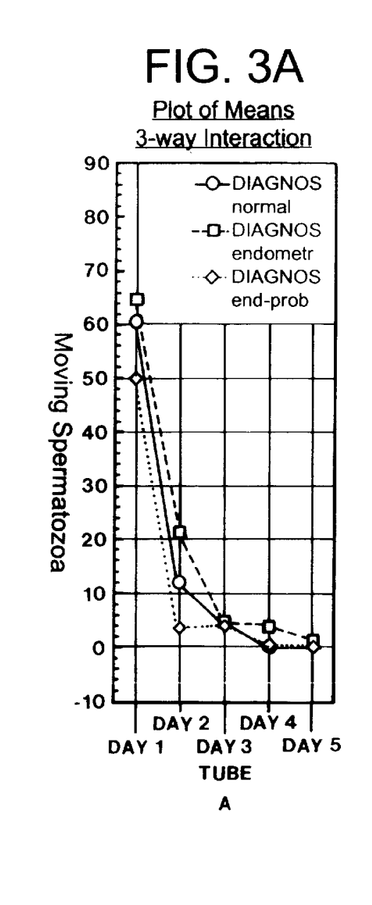
Figure 3B:
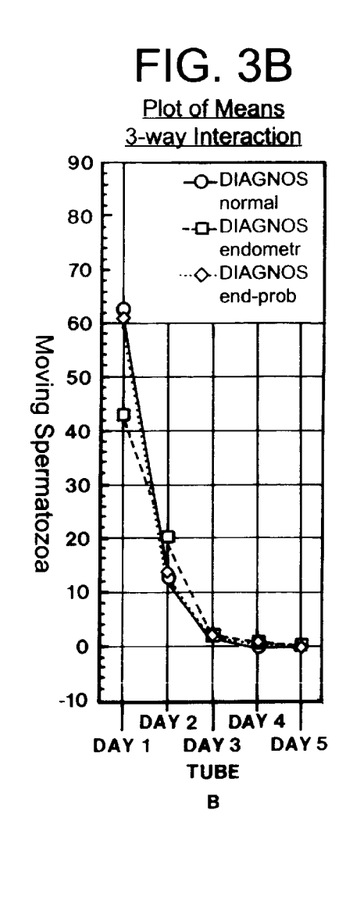
Figure 3C:
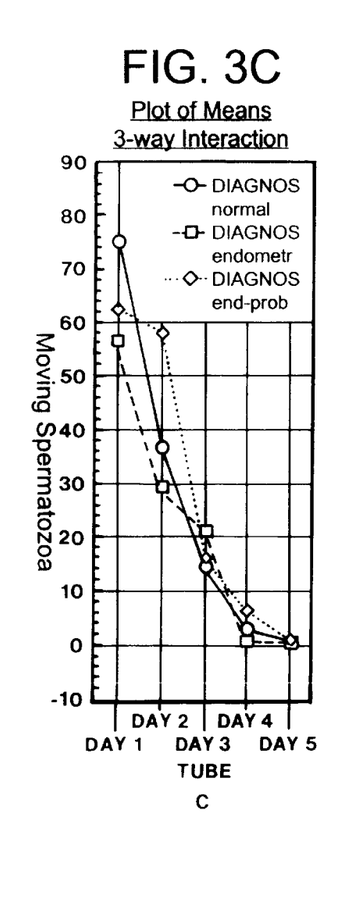
Figure 3D:
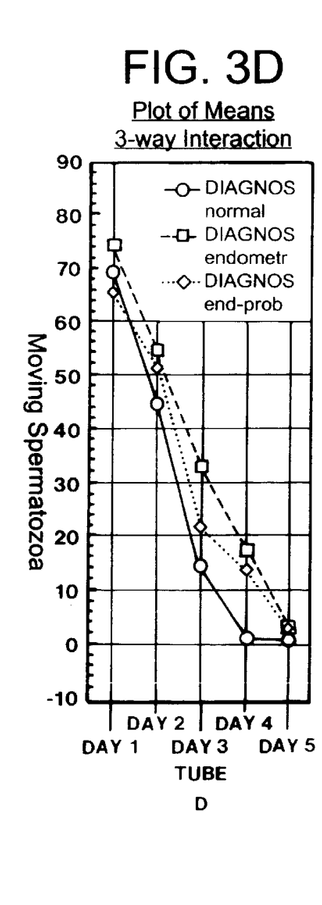
Figure 4A:
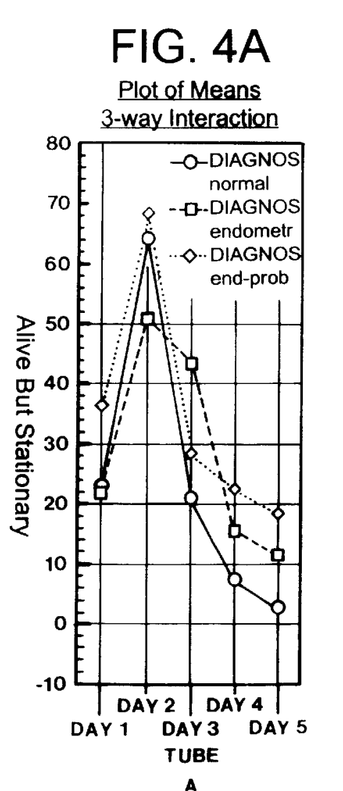
Figure 4B:
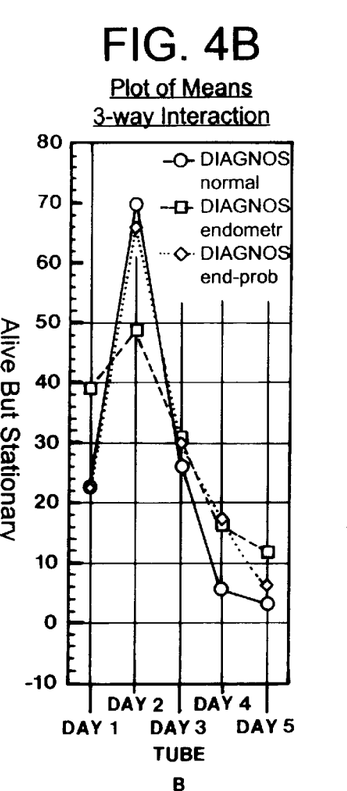
Figure 4C:
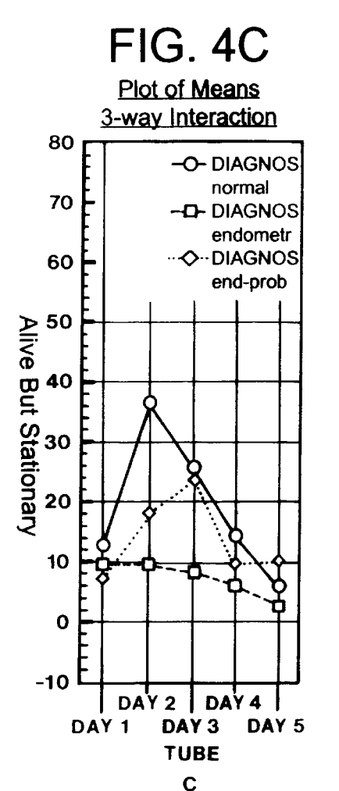
Figure 4D:
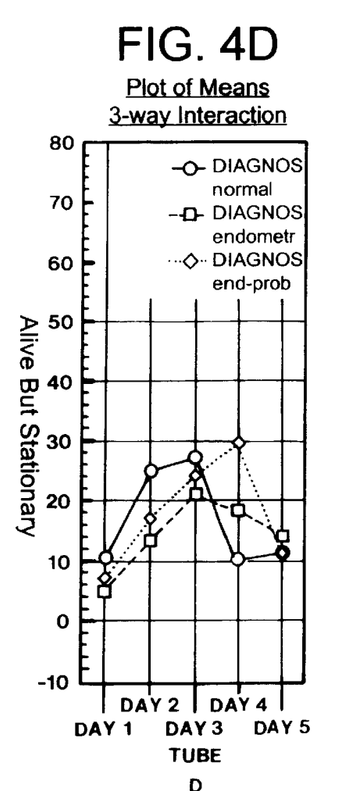
Figure 5A:
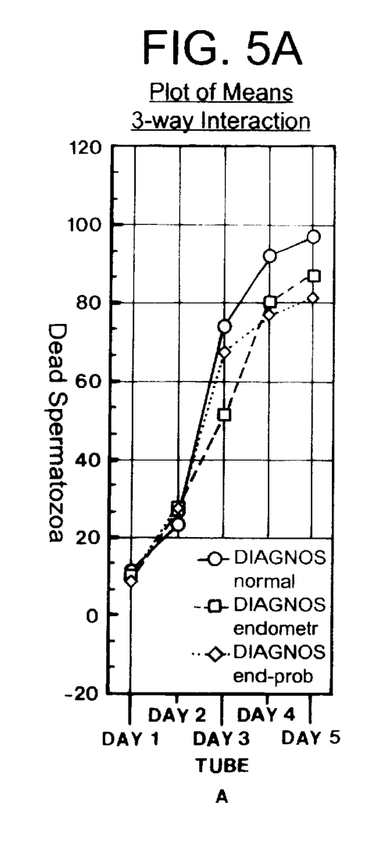
Figure 5B:
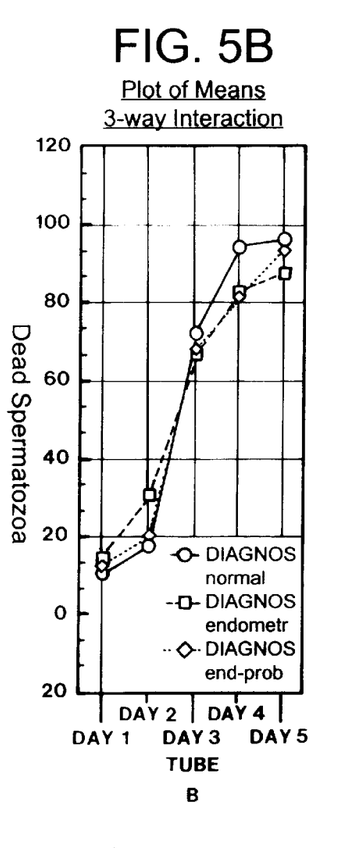
Figure 5C:
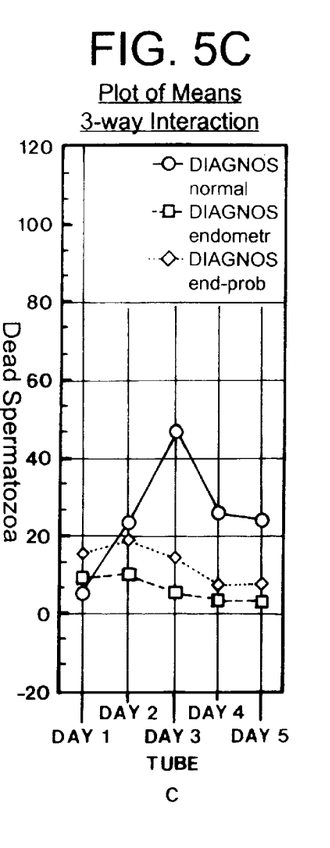
Figure 5D:
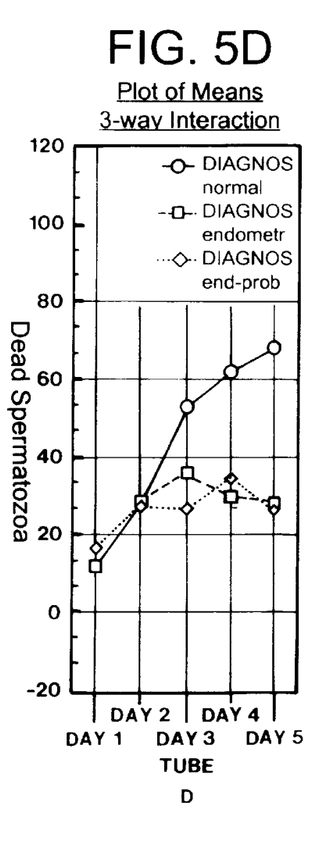

With reference to FIGS. 1–5, the use of a local anesthetic for the manufacture of a medicament for use against infertility or for increasing fertility. The local anesthetic may be selected from any substance that has a local anesthetic effect. Examples of such substances are bupivacaine (1-butyl-N-(2,6-dimethylphenyl)-2-piperidinecarboxamide), lidocaine (2-(dicthylamino)-N-(2,6-dimethylphenyl)acetamide), mepivacaine (N-(2,dimethylphenyl)-1-methyl-2-piperidinecarboxamide), prilocaine (N-(2-methylphenyl)-2-(propylamino)propanamide) and ropivacaine ((S)-N-(2,6-dimethylphenyl)-1-propy-2-pipendinecarboxamide). Other local anesthetics could also be used. Preferably lidocaine is used.

Another feature of the present invention is a pharmaceutical composition comprising a pharmaceutically effective concentration of a local anesthetic together with a pharmaceutically acceptable excipient. The concentration is one that has an effect on infertility of a woman or one that increases the fertility of a woman. The dose and concentration may be decided by the practician. The concentration of the effective substance is at least 5 μg/ml. One may use 100–2000 μg in 1–20 ml, preferably about 118 μg. The dose that is administrated is at least 100 μg, especially about 1000 μg. The composition is preferably administered in the peritoneal cavity, preferably by pertubation. The local anesthetic is defined as above.

The active ingredient can be mixed with excipients which are pharmaceutically acceptable and compatible with the active ingredient and in amounts suitable for use in the therapeutic methods described herein. In addition, if desired, the composition can contain minor amounts of auxiliary substances such as wetting or emulsifying agents, pH buffering agents and the like which enhance the effectiveness of the active ingredient.

The pharmaceutical composition of the present invention can include pharmaceutically acceptable salts of the components herein. Pharmaceutically acceptable salts include the acid addition salts that are formed with inorganic acid such as, for example, hydrochloric or phosphoric acids, or such organic acids as acetic, tartaric and mandelic acid.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, propylene glycol, polyethylene glycol and other solutes.

The composition may also comprise hyaluronan which is a viscous substance e.g. in gel formate. Hyaluronan gives a slow release of the active substance which is preferable as conception may take place up to 24 hours after ovulation and treatment according to the invention. Another advantage is that hyaluronan has a stimulating effect on the sperms (Zimmerman E R, Drobnis E, Robertson K R, Nakajima S T, Kim H: Semen preparation with the Sperm Select system versus a washing technique. Fertil Steril 1994; 61: 269–275).

Infertility is generally not being considered as an illness. The invention also embraces a process for treating infertility in a woman with a pharmaceutical composition according to the invention, characterized in that the pharmaceutical composition is inserted by pertubation.

The invention especially relates to a cosmetic or a non-therapeutic method against infertility or for increasing fertility wherein a) ovulation is diagnosed, b) a treatment with a local anesthetic is given when ovulation is expected according to step a).

The treatment is preferably done by pertubation. Preferably the steps are as follows:

Spontaneous ovulation: primary treatment during normal menstrual cycle. Stimulation only in anovulatory patients and primary with Clomifen (tablets) which is easy and inexpensive. One blood sample is needed postovulatory to confirm that there has been an ovulation during the treated cycle.

LH (luteinizing hormone) test: the LH-surge 24–36 hours prior to ovulation is diagnosed by self test at home of urine sample.

Pertubation: When the LH-test is positive a pertubation treatment is given with e.g. 10 ml of 100 μg/ml lidocaine in physiological NaCl or Ringer-solution during a normal gynecological examination. There will be no anesthesia needed.

Fertilization: No artificial treatment. The couple will try and achieve pregnancy by normal way by coitus at home after the pertubation treatment is given.

This absence of adverse effects on sperm survival finding demonstrates that the spermatozoa are unaffected by lidocaine which has also been demonstrated in other studies (Bennett S J, Bolton V, Parsons J. The effects of lignocaine on human sperm motility. J Assisted Reprod. & Genetics 1992; 9:271–3). It seems to be the case also for the oocytes since high levels of lidocaine have been measured without any problems with fertilization or embryo development (Bailey-Pridham D D, Cook C L, Reshef E, Hurst H E, Drury K, Yussman M A. Follicular fluid lidocain levels during transvaginal oocyte retrieval. Fertil Steril 1990; 53:171–173). The highest levels were 118 μg/ml which means that the dose of 1000 μg of lidocaine given in the in vitro incubations ought to be able to be used diluted to e.g. 100 μg/ml in 10 ml of isotone fluid. This concentration will now be used for a clinical study of pregnancy outcome after pertubation carried out 24 hours preovulatory to increase sperm survival.

Lidocaine has been used for many years without any reports of adverse effects during pregnancy as has also been shown in an animal study Ramazzotto J, Curro F A, Paterson J A, Tanner P, Coleman M. Toxicological Assessment of Lidocaine in the Pregnant Rat. J Dent Res 1985; 64:1214–1218) and should therefore be possible to use for treatment of infertility in the endometriotic patient The invention is illustrated by the following Example. All technical and scientific terms used are, unless otherwise defined, intended to have the same meaning as commonly understood by one of ordinary skill in the art. Techniques employed herein are those that are known to one of ordinary skill in the art unless stated otherwise. Publications mentioned herein are incorporated by reference.

EXAMPLE 1

Reduction of Phagocytosis of Spermatozoa in PF (Peritoneal Fluid) from Women with Endometriosis This study was undertaken to further analyze the function of the leukocytes in the reduced fertility during endometriosis and also search for a potential therapeutic approach. To exclude immunological influences only one sperm donor was participating in the experiments. Prepared sperm samples was incubated with non-centrifuged peritoneal fluid from healthy women and women with endometriosis to evaluate the importance of phagocytosis of spermatozoa on the reduced fecundity during endometriosis. The number of viable spermatozoa in the incubations were counted daily for five days with or without the presence of local anesthetics that was added in search of a method to reduce the activity of the peritoneal leukocyte populations.

Materials and Methods

Patients

Females The patients were divided into three different groups. The control material (n=9, mean age=38.5 years) consisted of women going through laparoscopic sterilization or women with unclear abdominal pain. The control cases had laparoscopic findings considered as normal with anatomically normal uterus and fallopian tubes.

The study group were women going: through laparoscopy to find the cause of infertility or of abdominal pain and where the diagnosis was endometriosis (n=11, mean age= 34.5 years). In this group the diagnose was laparoscopic in 8 patients and anamnestic probable endometriosis in 3 patients but who had not yet developed any endometriotic implants that could be seen at the laparoscopy.

Male The sperm donor was a healthy 38 year old male with normal fertility with an continence period of 2–3 days before each sperm sample. The sperm samples were prepared by the swim up technique to select the optimal population (Russel L D, Rogers B J. Improvement in the quality and fertilization potential of a human sperm population using the rise technique. J Androl 1987; 8:25).

Samples of Peritoneal Fluid Collected at Laparoscopy

After the patients had been anaesthetized, blood samples were taken for later analyses of hyaluronan, which in PF can be used as a marker of ongoing inflammation to exclude a PID (pelvic inflammatory disease). At the beginning of the laparoscopy with the instruments safely in the abdominal cavity, all obtainable peritoneal fluid in the Douglas' pouch was aspirated by a suction unit through a Teflon catheter (diameter 1.7 mm, Optinova, Godby, Finland) and mixed with 10 IU of Heparin/ml (Olive D L, Weinberg J B, Haney A F. Peritoneal macrophages and infertility: the association between cell number and pelvic pathology. Fertil Steril 1985; 44:772–777) in a Teflon bottle (Nalgene, Brochester, N.Y., USA) and immediately taken care of. The amount of peritoneal fluid were determined by weighing on an electric balance. Teflon was the material of choice for collecting the PF due to it's low adhesion of mammalian cells (Grinnell F, Milam M, Srere P A. Studies on cell adhesion. Arch Biochem Biophys 1972; 153:193–198). Heparin was used as anticoagulant to prevent the leukocytes from aggregating (Makarand et. al. 1985). Previously citrate has been used (Edelstam et al. 1994) which in the sperm incubation had adverse effects on sperm viability. All samples were taken after permissions from the patients and the sampling procedure was approved by the Ethical Committee, Faculty of Medicine, Uppsala University, Sweden.

Incubations of Spermatozoa and Peritoneal Fluid

Teflon vials were used for all incubations that were done in a humid cell incubator as follows:

a) cellmedium (1 ml), spermatozoa ($10^6$ in 1 ml cellmedium) and 0,1 ml NaCl.

b) cellmedium (1 ml), spermatozoa ($10^6$ in 1 ml cellmedium) and 0,1 ml lidocain 10 mg/ml (Xylocaine®, ASTRA).

c) spermatozoa ($10^6$ in 1 ml cellmedium), peritoneal fluid (1 ml) and 0,1 ml NaCl.

d) spermatozoa ($10^6$ in 1 ml cellmedium), 0,1 ml lidocain (10 mg/ml) and peritoneal fluid (1 ml).

Earls cellmedium (Sigma) with 0.35% BSA (bovine serum albumin) The remaining amount of peritoneal fluid was centrifuged and the supernatant frozen (–20° C.) for subsequent analyses of hyaluronan (Edelstam et al. 1994) The vials were analysed daily during five days and the following was counted in all the A–D incubations up to 100 spermatozoa:

number of free spermatozoa non-adherent to leukocytes number of spermatozoa with progressive motility number of spermatozoa with non-progressive movement number of spermatozoa that are stationary and alive number of dead spermatozoa Also the percentage of viable peritoneal leukocytes were noted daily with the use of Trypan blue.

Results

The main finding was that there were statistically significantly less phagocytised spermatozoa (p<0.02) in the vials when incubated with peritoneal fluid and lidocaine. The spermatozoa were observed caught in large aggregates of leukocytes and some apparently undergoing phagocytosis thus reducing the number of free functioning spermatozoa.

Spermsurvival with and without endometriosis After two days of incubation there where statistically significantly more free spermatozoa in the incubations with peritoneal fluid from the normal group compared to the group with endometriosis (Kruskal Wallis p<0.014).

Spermsurvival with and without lidocain No adverse effects were found on spermsurvival and there were statistically no significantly differences between the incubations of spermatozoa with or without lidocain after 24 or 48 hours. The p-values using Wilcoxon are shown in Table I and II respectively.

Spermsurvival with and without PF (peritoneal fluid) and lidocain, no concern of diagnosis The progressive motility is reduced more rapidly without the presence of peritoneal fluid (FIG. 2) compared to the incubation of spermatozoa alone.

Spermsurvival with and without PF and lidocain, in the endometriosis group In the presence of peritoneal fluid and lidocain there were significantly more free spermatozoa, especially after two days incubations in the endometriosis group. FIG. 1 and table II.

There were more dead spermatozoa in incubations with lidocain over time in both diagnosis groups. FIG. 5, table II.

Hyaluronan concentrations in peritoneal fluid exhibited no indications of ongoing inflammatory process, i.e. confirming all patients being healthy.

TABLE 1

P-values for the different parameters registered in the incubations when comparing with or without incubation with lidocain. Data after 24 hours incubation time.

| | Spermatozoa ±lidocain | Spermatozoa + PF Normal, ±lidocain | Spermatozoa + PF, endometr. ±lidocain | All patients without concern of diagnosis ±lidocain |
|---|---|---|---|---|
| free, non-adherent to leukocytes | — | All free with and without | 0.59 | 0.27 |
| progressively moving | 0.88 | 0.046 (a) | 0.67 | 0.11 |
| non-progress. movement | 0.59 | 0.59 | 0.79 | 0.58 |
| stationary | 0.76 | 0.40 | 0.31 | 0.18 |
| immobile (dead) | 0.28 | 0.14 | 0.09 | 0.024 (b) |
| Leukocyte viability | — | 0.26 | 0.29 | 0.92 |
| Spermatozoa adherent to leukocytes | — | No adherent to lukocytes in either group | 0.68 | 0.80 |

(a) more progressively moving spermatozoa in the incubations without lidocain.
(b) more dead in the lidocain group

TABLE II

P-values for the different parameters registered in the incubations when comparing with or without incubation with lidocain. Data after 48 hour incubation.

| | Spermatozoa ±lidocain | Spermatozoa + PF, Normal, ±lidocain | Spermatozoa + PF, endometr. ±lidocain | spermatozoa + PF without concern of diagnosis ±lidocain |
|---|---|---|---|---|
| free, non-adherent to leukocytes | — | 1.0 | 0.018 (d) | 0.0021 (d) |
| progressively moving | No progressively moving with or without lidocain | 1.00 | 0.89 | 0.95 |
| non-progress. movement | 0.18 | 0.025 (c) | 0.21 | 0.021 (c) |
| stationary | 0.78 | 0.26 | 0.58 | 0.22 |
| immobile (dead) | 0.50 | 0.038 (c) | 0.003 (c) | 0.00025 (c) |
| Leukocyte viability | — | 0.78 | 0.51 | 0.57 |
| Spermatozoa adherent to leukocytes | — | 1.00 | 0.53 | 0.63 |

(c) more in lidocain
(d) more free in the lidocain group

This investigation comprehend the impact of lidocaine on sperm survival and effect on the peritoneal leukocyte phagocytosis of spermatozoa in vitro during incubation for five days. This study has included only one donor of spermatozoa to avoid different immunological combinations which would have been uncontrolled factor in the experiments. Also this study follows the sperm survival for up to 5 days whereas previous studies have investigated the sperm survival during a 24 hour period. Further not only the number of free non-phagocytised spermatozoa was counted but also how many exhibited progressive or stationary movement as well as the number of alive, dead or free (i.e. not adhered to leukocytes) spermatozoa.

In this investigation, previous finding was confirmed that was described by Muscato et. al. 1982 concerning the reduced fertility in endometriosis patients due to sperm phagocytosis. Increased phagocytosis capacity of peritoneal macrophages from patients with endometriosis has also been demonstrated with fluorescent beads (Samejima T, Masuzaki H, Ishimaru T, Yamabe T. Activity of Peritoneal Macrophages in Endometriosis. Asia Oceania J Obstet Gynaecol 1989, 15:175–181).

Other studies of sperm phagocytosis have not considered the problem with loss of leukocytes that adhere to some material more that other (Grinnell et. al. 1972). Makarand et. al. 1985 used glass container for storage of peritoneal fluid. Glass has the highest adhesions of leukocytes (Grinell et. al. 1972) and has been used for separating macrophages (Smedsroed B, Pertoft H. Preparation of pure hepatocytes and reticuloendothelial cells in high yield from a single rat liver by means of Percoll centrifugation and selective adherence. J Leukocyte Biol. 1985; 38). Muscato et. al. 1989 has chosen polypropylene which is a better alternative than glass concerning the cell adhesions problem but less optimal than Teflon.

The finding of more dead spermatozoa in incubations with lidocaine over time must be considered as an effect of the reduced sperm phagocytosis in the presence of lidocaine, since there were, in incubations of spermatozoa alone with or without lidocaine, no adverse effects found on the spermatozoa. This must also be the explanation for the finding of increased non-progressively moving spermatozoa in the lidocaine incubations (FIG. 3). The reduction of progressive motility without the presence of peritoneal fluid might be an indication of that the PF (peritoneal fluid) contains substances necessary for the spermatozoa to maintain their function.

As mentioned in the introduction the fimbriae of the fallopian tubes are constantly moistured by peritoneal fluid which in the case of patients with endometriosis reduces the capacity of ovum pick up (Suginami et. al. 1986). As demonstrated in this and previous studies the leukocytes in the peritoneal fluid of patients with endometriosis are more potent in phagocytising spermatozoa (Muscato et. al. 1982). Thus women with endometriosis can have two factors contributing to their reduced fertility. This study has also indicated the possibility of using the effect of lidocaine in order to reduce the phagocytosis of spermatozoa.

In summary this study has demonstrated a reduced phagocytosis of spermatozoa in the presence of lidocaine. This phenomenon has to be followed up with randomized clinical trials of pertubations with saline or lidocaine/saline solutions preovulatory (LH-surge time).

While the present invention has been described in accordance with preferred compositions and embodiments, it is to be understood that certain substitutions and alterations may be made thereto without departing from the spirit and scope of the following claims.

I claim:

1. A method of reducing phagocytosis of spermatozoa in a woman to increase fertility in the woman, comprising the step of: administering a compound which acts as a local anesthetic to the woman in an amount sufficient for reducing phagocytosis of spermatozoa to increase the woman's fertility.

2. The method according to claim 1 wherein the compound which acts as a local anesthetic is selected from the group consisting of bupivacaine, lidocaine, mepivacaine, prilocaine, and ropivacaine.

3. A process for reducing phagocytosis of spermatozoa in a woman to increase fertility in the woman relative to the woman's present fertility, comprising the step of: administering a pharmaceutical composition to the woman, the pharmaceutical composition comprising a pharmaceutically effective concentration of a local anesthetic with a pharmaceutically acceptable excipient, the local anesthetic being in an amount sufficient for reducing phagocytosis of spermatozoa to increase the woman's fertility.

4. A method for reducing phagocytosis of spermatozoa in a woman to increase fertility in the woman relative to the woman's present fertility, comprising: administering to the woman a pharmaceutical combination composition comprising a local anesthetic, physiological NaCl and a hyaluronan in an amount effective to reduce phagocytosis of spermatozoa and to increase the woman's fertility, the local anesthetic being selected from the group consisting of bupivacaine, lidocaine, mepivacaine, prilocaine and ropivacaine, wherein the combination composition comprises at least five ug/ml of the local anesthetic.

5. The method according to claim 4 wherein the step of administering comprises the step of administering the pharmaceutical combination composition to the woman before ovulation of the woman.

* * * * *